United States Patent [19]

Krass

[11] Patent Number: 4,501,924

[45] Date of Patent: Feb. 26, 1985

[54] HERBICIDALLY ACTIVE SUBSTITUTED DIPHENYL ETHER ACETALS OR KETALS

[75] Inventor: Dennis K. Krass, Canal Fulton, Ohio

[73] Assignee: PPG Industries, Inc., Pittsburgh, Pa.

[21] Appl. No.: 490,818

[22] Filed: May 2, 1983

[51] Int. Cl.$^3$ ............................................. C07C 43/30
[52] U.S. Cl. ..................................... 568/592; 568/44; 564/347; 260/465 F; 71/98; 71/105; 71/124
[58] Field of Search .................. 568/592, 44; 564/347; 260/465 F; 71/98, 105, 124

[56] References Cited

FOREIGN PATENT DOCUMENTS

| 0053321 | 6/1982 | European Pat. Off. ............ 568/592 |
| 0056119 | 7/1982 | European Pat. Off. ............ 568/592 |
| 0064658 | 11/1982 | European Pat. Off. . |
| 3118371 | 11/1982 | Fed. Rep. of Germany ...... 568/592 |

*Primary Examiner*—Paul J. Killos
*Attorney, Agent, or Firm*—Edward J. Whitfield

[57] ABSTRACT

This invention relates to certain herbicidally active substituted diphenyl ether acetals or ketals, herbicidal compositions of the same and the use thereof for pre-emergence postemergence control of noxious plants, i.e., weeds.

4 Claims, No Drawings

HERBICIDALLY ACTIVE SUBSTITUTED DIPHENYL ETHER ACETALS OR KETALS

FIELD OF THE INVENTION

This invention relates to certain substituted diphenyl ether acetals or ketals and to the use of same to control the growth of noxious plants, i.e., weeds.

DESCRIPTION OF THE INVENTION

This invention provides herbicidally active substituted diphenyl ether acetal or ketal compounds represented by the Formula I:

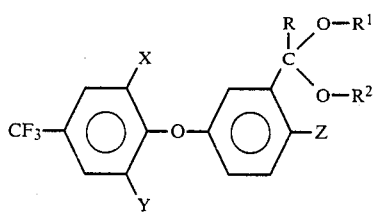

wherein:
X and Y are hydrogen or halogen provided that at least one of X or Y is halogen;
Z is nitro, halogen or cyano;
R is hydrogen or —$CH_2R^3$ wherein $R^3$ is hydrogen, halogen, $C_1$ to $C_3$ alkyl or haloalkyl, $C_1$ to $C_3$ alkoxy or alkylthio, mono or dialkylamino, or cyano; and
$R^1$ and $R^2$ are $C_1$ to $C_4$ alkyl.

Suitable alkyl radicals of which the various 'R' groups are representative include methyl, ethyl, n-propyl, isopropyl, n-butyl, t-butyl or isobutyl. Chloromethyl, chloroethyl, bromomethyl, bromoethyl, trifluoromethyl and the like are exemplary haloalkyls. As examples of alkoxy and alkylthio radicals there may be mentioned methoxy, ethoxy, propoxy, thiomethyl, thioethyl or the like. Mono or dialkyl amino groups include methylamino, dimethylamino, methylethylamino, diethylamino or the like. Halogens represented by X, Y, Z and R include bromine, chlorine or fluorine, preferably bromime or chlorine.

Preferred compounds of the Formula I are those wherein X is halogen, e.g., chlorine; Y is hydrogen and Z is nitro.

Compounds of the Formula I may be prepared using techniques known to and starting materials available to the art. For example, a Formula I compound may be prepared by reacting an appropriately substituted diphenyl ether aldehyde or ketone of the Formula II:

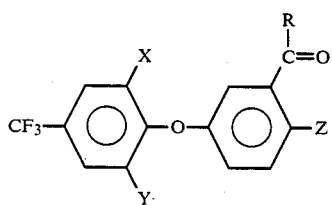

wherein X, Y, Z and R are as previously defined, with an aliphatic monoalcohol. Compounds of the Formula II are disclosed, e.g., in U.S. Pat. No. 4,344,789; whereas methanol, ethanol, propanol, butanol, and the like are exemplary of suitable monoalcohols.

The following Example is illustrative of the preparation of certain compounds of this invention.

EXAMPLE I

Preparation of 5-(2-chloro-4-trifluoromethylphenoxy)-2-nitrobenzaldehyde dimethyl acetal A 250 milliliter flask was charged with 2.0 grams of 5-(2-chloro-4-trifluoromethylphenoxy)-2-nitrobenzaldehyde, 150 milliliters of methanol and a few crystals of p-toluene sulfonic acid. The stirred reaction mixture was then heated to reflux. After refluxing for about 20 hours, the reaction mixture was cooled and made basic with 1.67 percent aqueous sodium carbonate solution. Methanol was stripped under vacuum and the aqueous solution was twice extracted with chloroform. The combined chloroform extracts were washed with saturated aqueous sodium chloride solution and dried over anhydrous magnesfum sulfate. Subsequent filtration and evaporation of solvent afforded 1.93 grams of a dark brown oil identified by NMR, IR and MS analyses as 5-(2-chloro-4-trifluoromethylphenoxy)-2-nitrobenzaldehyde dimethyl acetal.

Although the invention has been illustrated by the foregoing Examples with regard to the preparation of specific compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the growth medium, e.g., soil, before emergence of weeds therefrom, or to the plant surface subsequent to emergence from the growth medium, a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.5 to 2.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyrazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, e.g., in the *Herbicide Handbook of the Weed Society of America* may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation wil be surface applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled, combated, or eliminated are, e.g., annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail ironweed, sesbania, cattail, wintercress, horsenettle, nutsedge, milkweed, sicklepod, and the like.

The compound prepared as described in the example was tested for herbicidal efficacy, against a variety of broadleaf and grassy weed species, under controlled laboratory conditions of light, humidity and temperature. Solvent solutions of the compound were applied, both preemergence and postemergence, to test flats containing the various weed species, and herbicidal efficacy was determined by visual inspection, periodically after application of the compounds. Herbicidal efficacy was determined on a linear scale of from 0 (no injury) to 10 (all plants dead). More particularly, the compound of the Example was found effective, at a rate of application of 2.0 pounds per acre in preemergence control of teaweed, wild mustard, coffeeweed, velvetleaf and tall morningglory, herbicidal injury ratings typically ranging from 7 to 8 having been observed up to 21 days subsequent to application.

At a postemergence rate of application of 2.0 pounds per acre, the compound of the Example was found effective, particularly against broadleaved weeds, i.e., teaweed, jimsonweed, wild mustard, coffeeweed and velvetleaf, herbicidal injury ratings typically ranging from 7 to 10 having been observed up to 21 days subsequent to application.

Although the invention has been described in considerable detail by the foregoing, it is to be understood that many variations may be made therein by those skilled in art without departing from the spirit and scope thereof as defined by the appended claims.

I claim:

1. A compound represented by the formula:

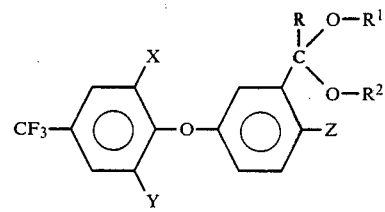

wherein:
X and Y are hydrogen or halogen provided that at least one of X or Y is halogen;
Z is nitro, halogen or cyano;
R is hydrogen or —CH$_2$R$^3$ wherein R$^3$ is hydrogen, halogen, C$_1$ to C$_3$ alkyl or haloalkyl, C$_1$ to C$_3$ alkoxy or alkylthio, mono or dialkylamino, or cyano; and
R$^1$ and R$^2$ are C$_1$ to C$_4$ alkyl.

2. A compound of claim 1 that is 5-(2-chloro-4-trifluoromethylphenoxy)-2-nitrobenzaldehyde dimethyl acetal.

3. A herbicidal composition containing an inert carrier and a herbicidally effective amount of a compound or mixture of compounds defined in claim 1.

4. In a method of controlling weeds wherein a herbicidally effective amount of herbicide is applied to a growth medium prior to emergence of the weeds therefrom or to the weeds subsequent to their emergence from the growth medium, wherein the improvement resides in using as the herbicide a compound or mixture of compounds defined by claim 1.

* * * * *